(12) United States Patent
Kassab et al.

(10) Patent No.: US 8,663,196 B2
(45) Date of Patent: Mar. 4, 2014

(54) ENDOVASCULAR SHEATH WITH GRADABLE STIFFNESS DEVICE AND METHOD

(75) Inventors: Elias Habib Kassab, Grosse Pointe Shores, MI (US); Mark Edwin Zyzelewski, Kalamazoo, MI (US)

(73) Assignee: Kassab Kughn Endovascular Devices LLC, Farmington, MI (US)

(*) Notice: Subject to any disclaimer, the term of this patent is extended or adjusted under 35 U.S.C. 154(b) by 1015 days.

(21) Appl. No.: 12/235,894

(22) Filed: Sep. 23, 2008

(65) Prior Publication Data
US 2010/0076405 A1 Mar. 25, 2010

(51) Int. Cl.
*A61M 25/00* (2006.01)
*A61M 25/06* (2006.01)

(52) U.S. Cl.
CPC ......... *A61M 25/0053* (2013.01); *A61M 25/005* (2013.01); *A61M 25/0051* (2013.01); *A61M 25/0054* (2013.01); *A61M 2025/0063* (2013.01); *A61M 2025/0681* (2013.01)
USPC ........... 604/525; 604/523; 604/524; 604/526; 604/527; 604/528; 604/530; 604/531; 604/532

(58) Field of Classification Search
CPC .......... A61M 25/005; A61M 25/0045; A61M 25/0051; A61M 25/0053; A61M 25/0054; A61M 25/01; A61M 2025/0058; A61M 2025/0063; A61M 2025/0681; A61B 1/00078
USPC ........................ 604/158, 523–528, 530–532
See application file for complete search history.

(56) References Cited

U.S. PATENT DOCUMENTS 4,516,972 A 5/1985 Samson
5,290,229 A * 3/1994 Paskar ........................ 604/95.04

(Continued)

FOREIGN PATENT DOCUMENTS

EP 1316327 B1 6/2006
EP 1716822 A1 11/2006

(Continued)

OTHER PUBLICATIONS

Seldinger SI, Catheter Replacement of the Needle in Percutaneous Arteriography; a New Technique, Acta Radiologica (5); 368-76 (1953).

(Continued)

*Primary Examiner* — Bhisma Mehta
*Assistant Examiner* — Larry R Wilson
(74) *Attorney, Agent, or Firm* — Brooks Kushman P.C.

(57) ABSTRACT

An endovascular sheath apparatus 2 is provided. The endovascular sheath apparatus 2 includes an inner tube 12 that includes a lumen 26 for introducing medical fluids or devices and an outer surface. The apparatus 2 further includes an outer tube 22 with an interior surface. The outer and inner surfaces define a cavity 28 therebetween. The apparatus 2 still further includes a stiffening component 20 which in one embodiment includes a braided material that is at least partially received in at least part of the cavity 28. An actuating mechanism 18 cooperates with the stiffening component 20. A method of providing intravascular delivery of a sheath includes the steps of providing an inner tube 12; positioning a stiffening component 20 around the inner tube 12; and deploying an actuating mechanism 18 that cooperates with the stiffening component 20, a stiffness characteristic of which being adjustable extra-corporeally by movement of the actuating mechanism in combination with the stiffening component.

26 Claims, 13 Drawing Sheets

(56) References Cited

U.S. PATENT DOCUMENTS

| | | | |
|---|---|---|---|
| 5,599,326 | A | 2/1997 | Carter |
| 6,447,475 | B1 * | 9/2002 | Castellano ............... 604/68 |
| 6,511,471 | B2 * | 1/2003 | Rosenman et al. .......... 604/528 |
| 7,226,466 | B2 | 6/2007 | Opolski |
| 7,273,487 | B1 | 9/2007 | Duchamp et al. |
| 7,309,334 | B2 * | 12/2007 | von Hoffmann ............ 604/524 |
| 2004/0049157 | A1 * | 3/2004 | Plishka et al. ........... 604/164.09 |
| 2006/0106447 | A1 * | 5/2006 | Opolski ................... 623/1.11 |
| 2006/0129130 | A1 * | 6/2006 | Tal et al. ................ 604/525 |
| 2006/0184105 | A1 | 8/2006 | Townsend et al. |
| 2006/0235502 | A1 | 10/2006 | Belluche et al. |
| 2006/0258987 | A1 | 11/2006 | Lentz et al. |
| 2006/0264907 | A1 | 11/2006 | Eskridge et al. |
| 2006/0270980 | A1 | 11/2006 | Menzi et al. |
| 2007/0049899 | A1 | 3/2007 | Chambers |
| 2007/0060880 | A1 * | 3/2007 | Gregorich et al. ......... 604/96.01 |
| 2008/0045895 | A1 | 2/2008 | Simpson et al. |
| 2008/0058722 | A1 | 3/2008 | Von Oepen et al. |
| 2008/0172037 | A1 | 7/2008 | Huang et al. |

FOREIGN PATENT DOCUMENTS

| | | |
|---|---|---|
| WO | 9856447 A1 | 12/1998 |
| WO | 2008057839 A2 | 5/2008 |

OTHER PUBLICATIONS

International Search Report, International application No. PCT/US2009/057380, date of mailing Nov. 4, 2009.

* cited by examiner

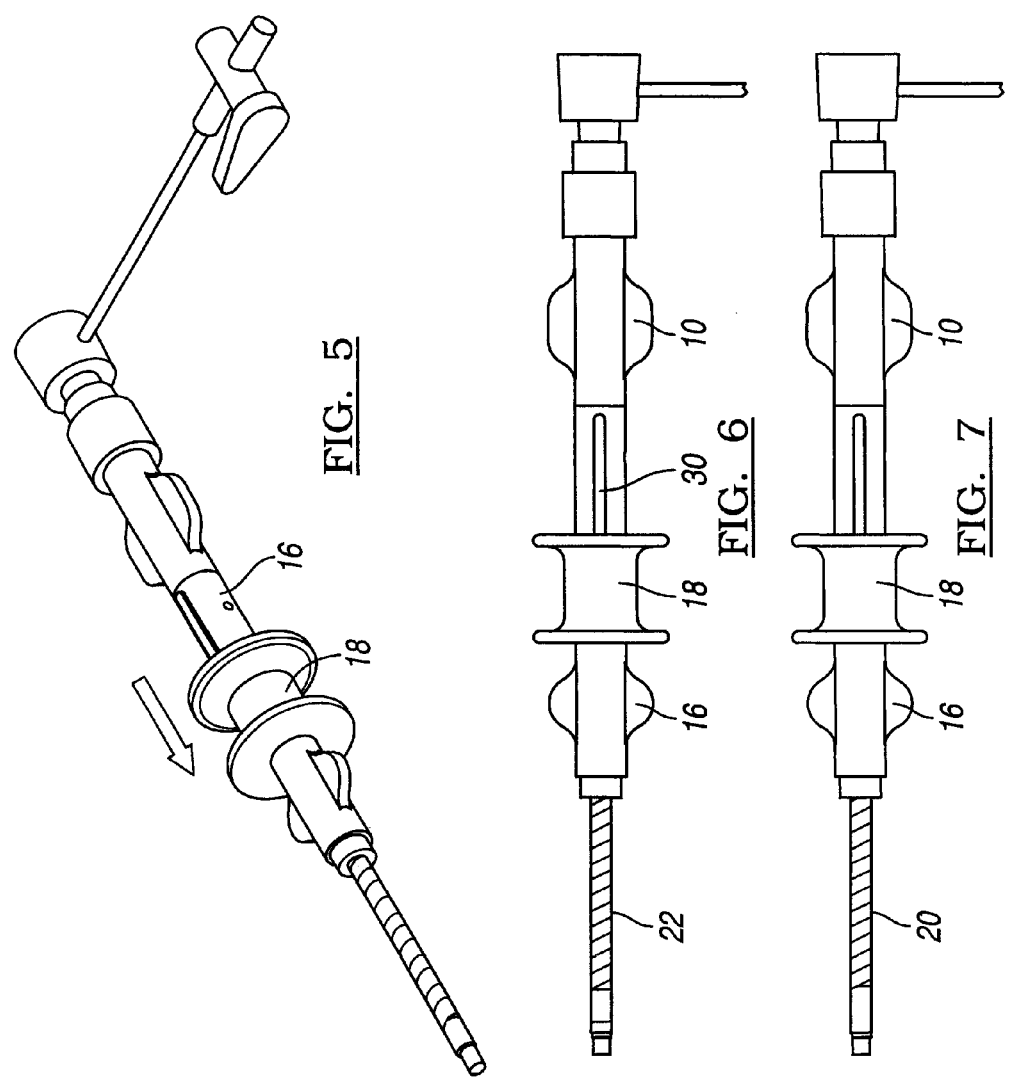

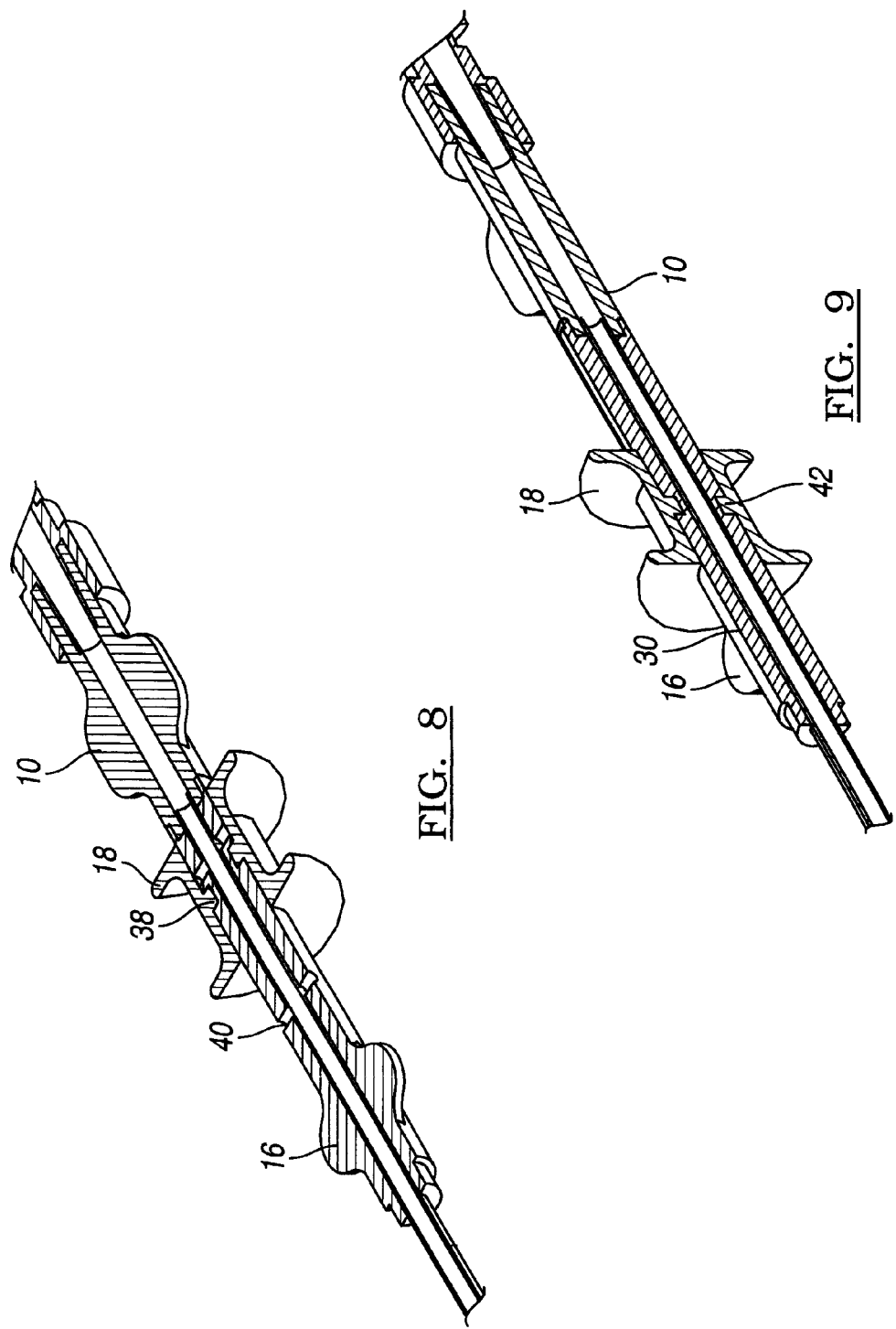

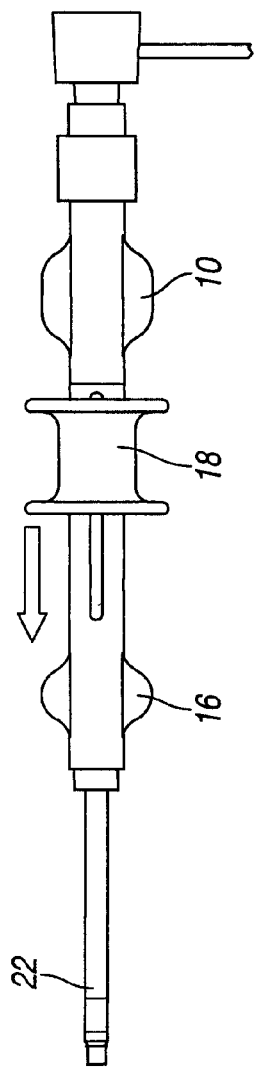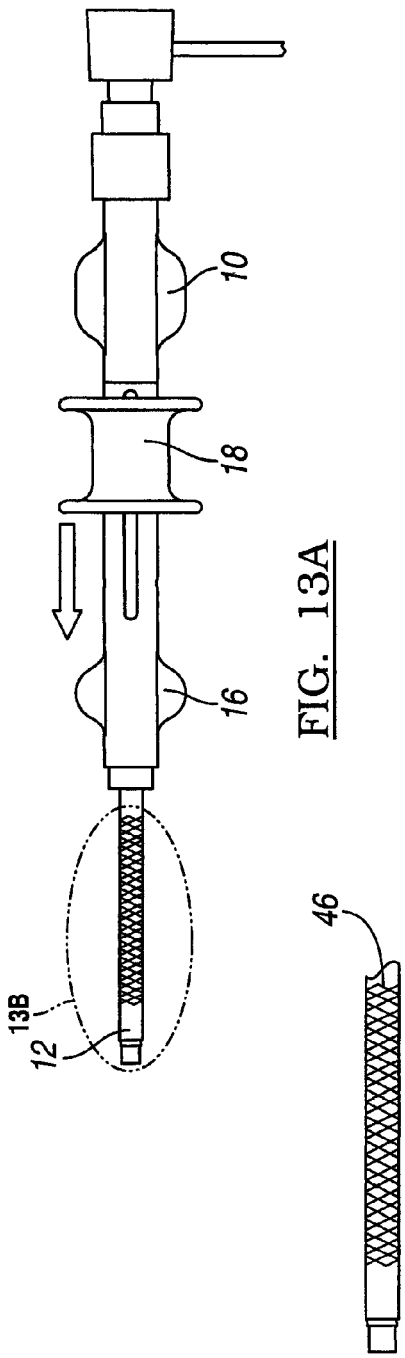
FIG. 12
FIG. 13A
FIG. 13B

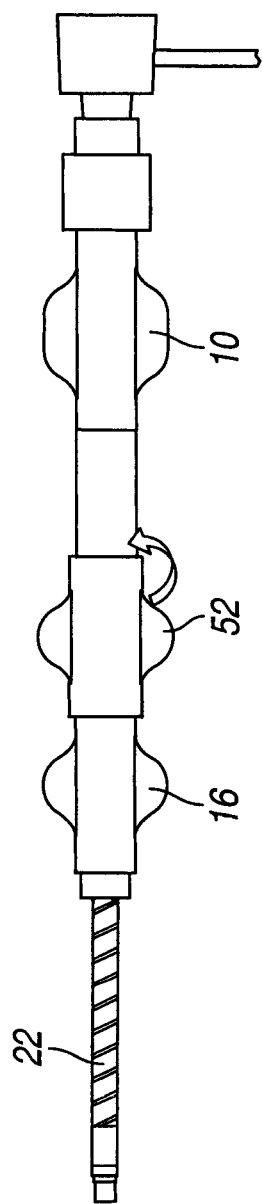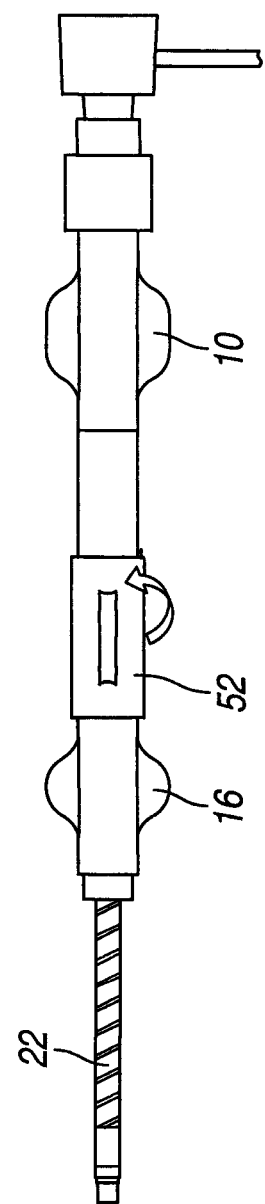

ENDOVASCULAR SHEATH WITH GRADABLE STIFFNESS DEVICE AND METHOD

BACKGROUND OF THE INVENTION

1. Field of the Invention

The invention relates to a sheath device with gradable stiffness and method that reduces or prevents buckling when inserted into a vascular tract.

2. Background Art

Endovascular surgery has developed as a form of minimally invasive surgery that is used to access many regions of the body through major blood vessels. Conventionally, a catheter is introduced through the skin into a large blood vessel such as the femoral artery or vein. Often, the catheter carries a radio-opaque dye that can be detected by X-ray or fluoroscopic procedures. Endovascular surgery is becoming more widely used because it is minimally invasive and offers immediate advantages over more traditional, yet highly invasive surgeries.

Generally stated, a catheter is a tube that can be inserted into a body cavity, duct or vessel. Catheters typically allow drainage or the injection of a fluid or access by surgical instruments. Many uses require that the catheter be thin and flexible (a "soft" catheter or tube); in other cases it may be a larger solid tube—a "hard" catheter.

As used herein, (1) the term "sheath" refers to the outer covering of a guide wire. Unless the context dictates otherwise, it may be used interchangeably with the term "catheter," and (2) the term "guide wire" refers to a long and flexible fine spring that is used to introduce and position an intravascular catheter. Conventionally, the catheter or sheath is often threaded over the wire—the wire may then be withdrawn, leaving the catheter in place, as taught by the Seldinger technique, a medical procedure that is used to obtain access to blood vessels and other hollow organs. Seldinger S1 (Catheter Replacement of the Needle in Percutaneous Arteriography; a New Technique). *Acta Radiologica* (5); 368-76 (1953).

During interventional vascular procedures, situations may arise where a catheter needs to be advanced through tortuous paths, in which it may be difficult to steer a guide wire or other interventional device along the interstices a vessel. For example, one area in the vascular geometry that causes issues related to advancing a device is the interface of the femoral and aortic vessels. During peripheral procedures, the entry location for devices is the femoral artery on the side of the body opposite the area of concern. The device must then pass over the femoral arch and into the opposite femoral artery. When the interventional devices used during the procedure advance towards such tortuous anatomy, buckling of the device often occurs at the femoral/aortic interface. Typically, conventional interventional devices tend to buckle under the axial force reaction of the tortuous vessel to the pressures of insertion. Buckling of the device often occurs proximal to the tortuous anatomy.

There are several reasons why this situation is difficult to overcome with current technology:

1. The geometry of a guide wire. A guide wire must have some flexibility to be able to steer through the vascular anatomy without dissecting a vessel. A guide wire is typically a small diameter wire (0.014") and is pliable and soft. When the guide wire is advanced through any tortuous anatomy, due to the small size of the wire, the wire has little ability to resist buckling. The proximal section of the wire typically buckles, and very little if any force is transmitted to the distal end of the wire.

2. The flexibility of the guiding catheter or sheath. Guiding catheters and sheaths are conventionally made from reinforced extruded plastic tubing. These devices are soft and generally provide little resistance to buckling.

3. The intervention devices that are used during the procedure. The intervention devices (e.g. stent delivery systems and balloons) are pliable along their axial shaft, and easily buckle when an axial force is applied.

Most devices and techniques that are available do not provide a solution to the buckling that occurs when tortuous anatomy is encountered during a procedure. If a device can not be advanced through this tortuous anatomy, the procedure may not be able to be performed, and the outcome for the patient may be compromised.

It is known that when the leading edge of a sheath encounters a tight lesion, there is a loss of kinetic energy. Some approaches solve this problem by using a hydrophilic material that is applied to the sheath. The problem with this approach, however, is that the surgeon's hands tend to slip over the outside surface of the sheath.

Among the U.S. and foreign patent documents that were considered before filing this application are the following: EP131632; EP171682; WO98/5644; U.S. Pat. Nos. 5,599,326; 7,226,466; 7,273,487; 20060235502; 20060258987; 20060264907; 20070049899; 20080045895; 20080172037.

SUMMARY OF THE INVENTION

Against this background it would be desirable to have a sheath device with a simple design, that is easy to use in patients that require an interventional vascular procedure. Preferably, such a sheath device would be intuitive to use and require minimal surgical finesse, yet be able to negotiate a tortuous path that may include calcified lesions and fibrosed areas, swiftly and with repeatability if desired without disrupting adjacent tissue.

Preferably, the disclosed sheath device reduces the risk of vascular perforation by offering a tip design that does not ablate tissue ahead of its distal end, thereby avoiding inadvertent rupture of tissue that may be inadvertently contacted.

In one aspect, the invention includes a device and method that reduces or prevents unwanted buckling of interventional devices. The inventive device allows the transmission of axial forces through the interventional devices to the distal end of the product without kinking or buckling.

It would be desirable to have a differential level of stiffness along the length of a sheath. For example, the distal region of the sheath would desirably be fluffy or soft. This would reduce the risk of trauma that might otherwise be caused by interference between the distal end of the sheath and a tight turn in an arterial wall.

Preferably, the surgeon would like to be able to determine without interchanging sheaths whether a particular sheath would be stiff or not stiff (compliant) an intermediate region or in a region proximate its distal end. Thus, one aspect of the invention includes a sheath that has a changing modulus of elasticity along its length. In some embodiments, the sheath may have a modulus of elasticity along its length that could be discretely or gradually changed.

Another facet of the invention is the provision of a sheath that has the capability to change its outside diameter along its length so that, for example, the outside diameter may be less at the distal than at the proximal end. These facets may also have applicability to designing a stent.

To meet these needs, an endovascular sheath apparatus is provided that comprises an inner tube which includes a lumen for introducing medical fluids or devices and an outer surface.

Disposed outside the inner tube is an outer tube that has an interior surface. The respective outer and inner surfaces define a cavity therebetween. A stiffening component is at least partially received in at least part of the cavity. Cooperating with the stiffness component is an actuating mechanism.

BRIEF DESCRIPTION OF THE DRAWINGS

FIG. 5 depicts a distal portion of the sliding mechanism in a "stiff" position (isometric view);

FIG. 6 depicts a proximal position of the sliding mechanism including the outer tube (side elevation view);

FIG. 7 depicts a proximal position of the sliding mechanism with the helical tube stiffening component, in which the outer tube is hidden and in which a helix is configured in a closed condition (side elevation view);

FIG. 8 depicts a slide mechanism that cooperates with locking detents for "soft" and "stiff" positions (sectioned, isometric view);

FIG. 9 depicts a sliding mechanism including an outer tube hub sliding track, in which a tracking tab is shown in a sliding position and a linear track is provided in an outer tube hub (sectioned, isometric view);

FIG. 12 depicts a proximal position of the sliding mechanism and outer tube (side elevational view);

FIGS. 13A and 13B depict a proximal position of the sliding mechanism that cooperates with an embodiment of a braided tube stiffening component, with the outer tube hidden (side elevation view);

FIG. 16 depicts an "open" position ("soft") of a rotational handle (Embodiment #3, side elevation view);

FIG. 17 depicts this embodiment with the rotational handle rotated to a "stiff" position ("closed"; side elevation view);

DETAILED DESCRIPTION OF THE PREFERRED EMBODIMENT(S)

Figure 1:
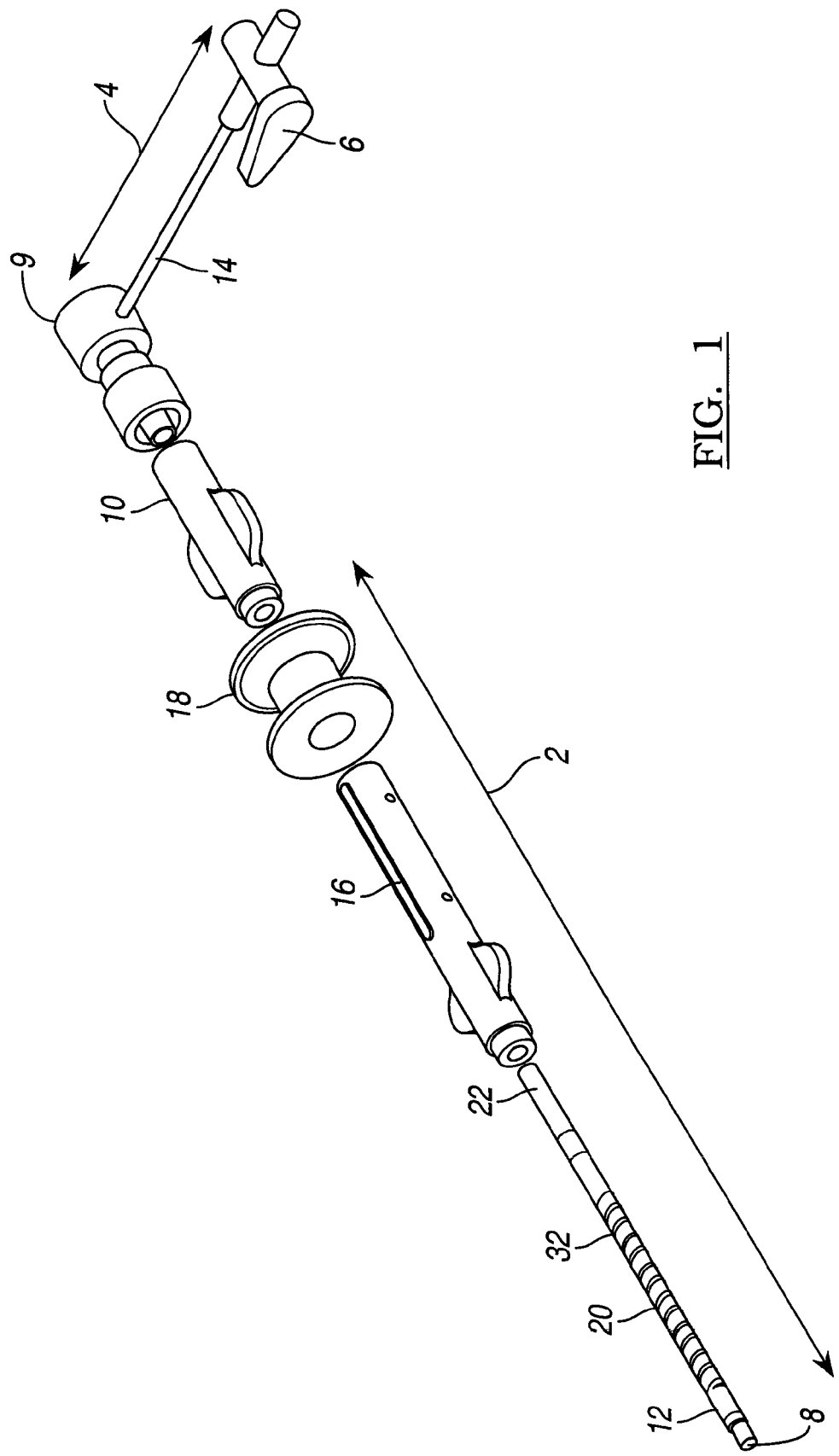
FIG. 1 is an overall perspective, exploded view of several aspects of the invention (Embodiment #1)
Figure 2:
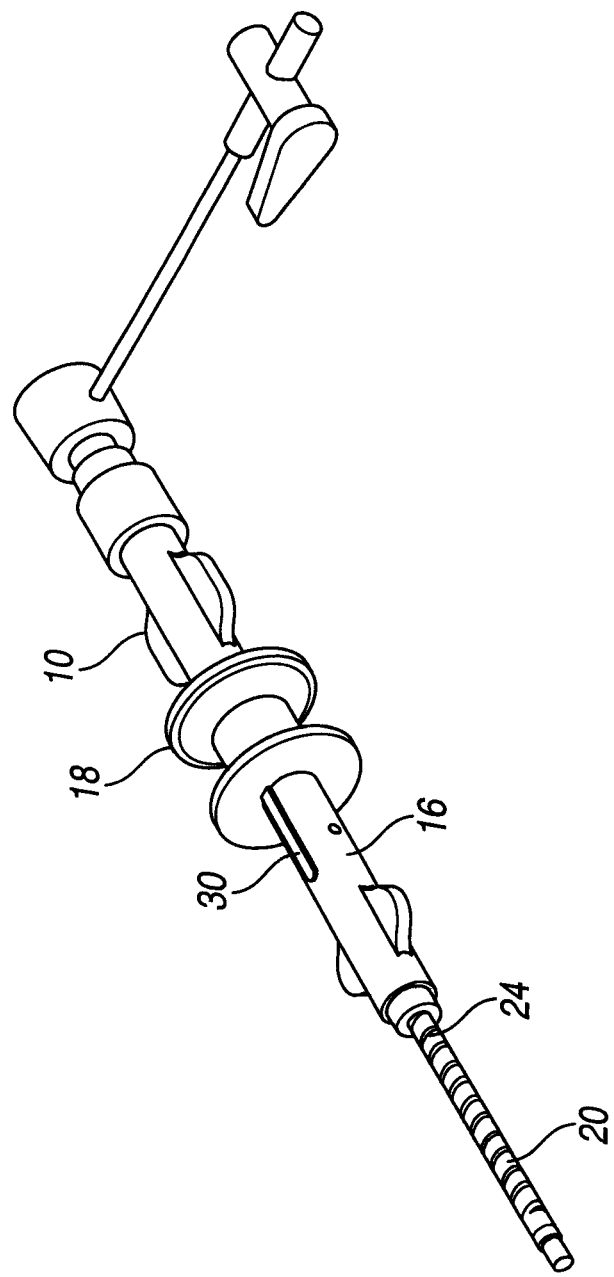
FIG. 2 depicts a proximal position of a sliding mechanism (isometric view) when the device is in a "soft" position.
Figure 3:
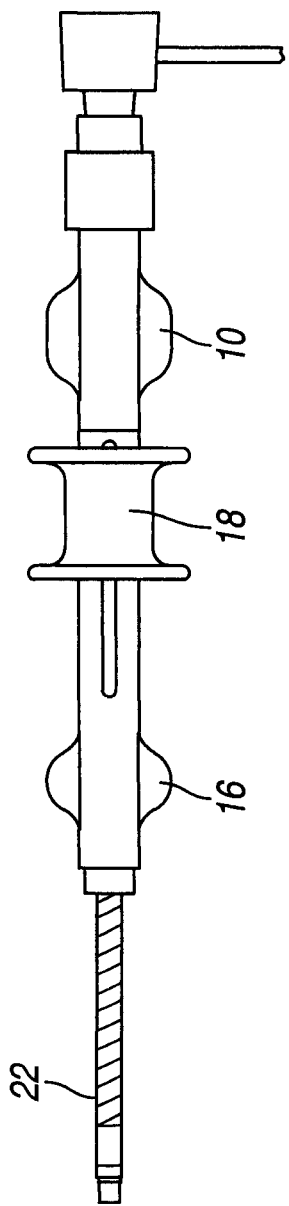
FIG. 3 depicts a proximal position of a sliding mechanism with an outer tube (side elevation view)

Turning first to FIGS. 1-3 of the drawings, there is depicted an endovascular sheath apparatus 2 that has an inner tube 12 which includes a lumem 26 for introducing medical devices or fluids. The inner tube 12 has an outer surface 13 (best seen in FIGS. 28-29.) Positioned outside the inner tube 12 is an outer tube 22 that has an interior surface 23. Lying between the inner 23 and outer 13 surfaces is a cavity 28. At least a portion of the cavity 28 houses a stiffening component 20 that reinforces at least a portion of the inner tube 12 to minimize or prevent kinking. In cooperation with the stiffening component 20, there is provided an actuating mechanism 18. The cavity 28 lies between the inner 12 and outer 22 tubes for placement of a tube stiffening component 20.

As used herein, the terms "proximal" and "distal" describe the opposing axial ends of the endovascular sheath assembly 2 as well as the axial ends of a medical device with which the sheath is used, and its components. The term "proximal" refers to the end of the member (or component) that is closest to the surgeon during use. Conversely, the term "distal" refers to the end of the member (or component) that is positioned closest to the end of the sheath assembly 2 that is initially inserted into the vascular system.

In its environment of use, the endovascular sheath 2 may include an inner tube hub 10 (FIGS. 1-2), the proximal section of which it may if desired be attached to a valve system 6. In one embodiment, the valve system 6 may serve as a one-way valve 14 by which fluid or device may be ducted into the inner tube 12. If desired, the one-way valve 6 may be incorporated into the inner tube hub 10. As illustrated in FIGS. 1-9, a hub section 10 optionally lies at an interface of the sheath assembly 2 with other interventional devices 4. In each design contemplated (FIGS. 1-29), the one-way valve 14 may optionally serve as a secondary piece. This valve prevents the flow of blood out of the device, but allows the introduction of interventional devices (guide catheters, wires, etc.) into the vasculature. It may also be a multiple piece design with a removable valve. The proximal section also optionally has a luer lock connection for flushing the device or injecting fluids into the system such as contrast-providing media.

Preferably, the outer tube 22 provides a smooth exterior surface to facilitate navigation along tortuous and possibly narrowing channels in the vascular system. In practice, a bond 15 (FIG. 28) may be provided at a distal region of the outer tube 22 in order to affix it to the inner tube 12.

If desired, an outer tube hub 16 (FIGS. 1-2) may be attached to the outer tube 22. The outer tube hub 16 attaches to the inner tube hub 10.

Continuing with primary reference to FIGS. 6-9, the outer tube hub 16 provides a track 30 that guides in one embodiment the linear displacement of an actuating or sliding mechanism 18. Preferably, the track 30 defines one or more locating features which in the embodiment depicted in FIG. 8 include (in Embodiment #1 of the stiffening component 20) a detent 40 (distal, stiff) and a position 38 (proximal, soft). In the embodiment of FIG. 9, a tracking tab 42 is guided along the track 30 that is provided in the outer tube hub 16. If desired, the actuating mechanism 18 may be positioned at an intermediate location if the surgeon desires the inner tube 12 to have a stiffness which is intermediate between that which results from positioning the actuating mechanism at locations 40 or 38.

It will thus be appreciated that the actuating mechanism 18 communicates with a stiffening component 20 (FIGS. 10-11, Embodiment #2) and interfaces with the outer tube huh 16 (FIGS. 1-2). The stiffening component 20 has a distal end 8 that is affixed by bond 15 to the inner tube 12 at one end and to the actuating mechanism 18 at a proximal end of the stiffening component 20.

The inner tube 12 of the sheath assembly 2 conventionally includes a reinforced tubular section that is typically made of an extruded plastic. It is soft and pliable. The distal tip is preferably extremely soft to reduce the possibility of any vessel damage when the device 2 is introduced into an artery, such as the femoral artery. In one embodiment of the disclosed invention, the body of the inner tubular section 12 is reinforced with the stiffening component 20, such as a braided material in Embodiment #2, preferably made of metal or strands of a plastic material. This helps prevent the tubular section 12 from susceptibility 60 being kinked, and gives a selective stiffening characteristic to the device 2 that resists buckling.

One objective of the inventive design is to retain the functionality of the current products on the market, but give the interventionalist a sheath assembly 2 that has adjustable stiffness when required or desirable during the procedure.

The inventive design incorporates variations in the stiffening component 20 of the sheath assembly 2. These variations help stiffen the body of the inner tubular section 12 of the sheath. This stiffening allows the interventionalist to more easily transmit axial force when desired to the distal end 8 of the device, thereby facilitating the passage of the device 2 through a tortuous anatomy.

There are at least four alternative embodiments of the inventive concept:

Embodiment #1

Helical Stiffening Component with Linear Slide

Figure 19:
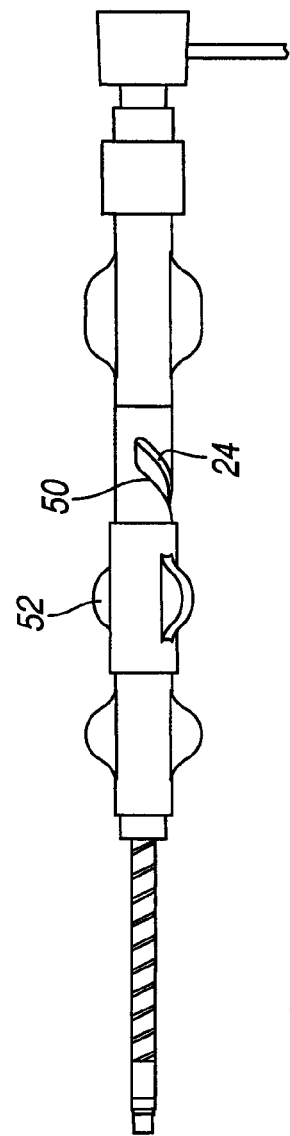
FIG. 19 depicts a helical rotation in which the handle has moved (with both rotational and linear movement) to a "stiff" position ("closed")
Figure 20:
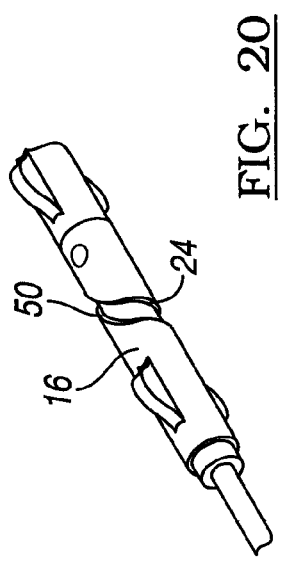
FIG. 20 depicts a helical track in the outer tube hub (isometric view)
Figure 21:
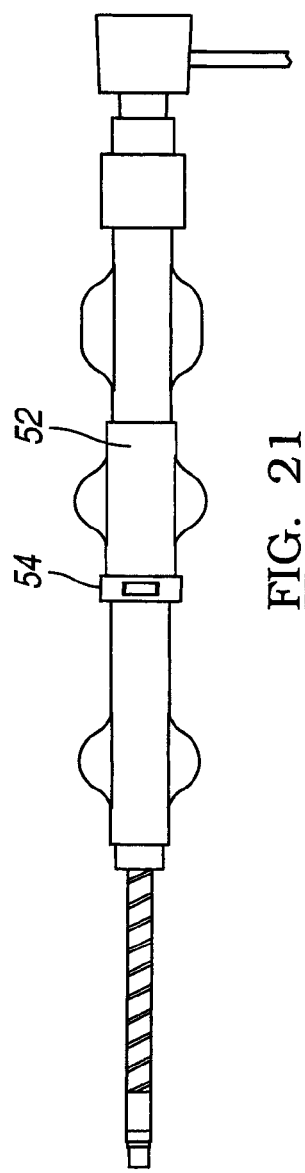
FIG. 21 depicts an optional safety mechanism that prevents accidental movement of the sliding mechanism (side elevation view)
Figure 23:
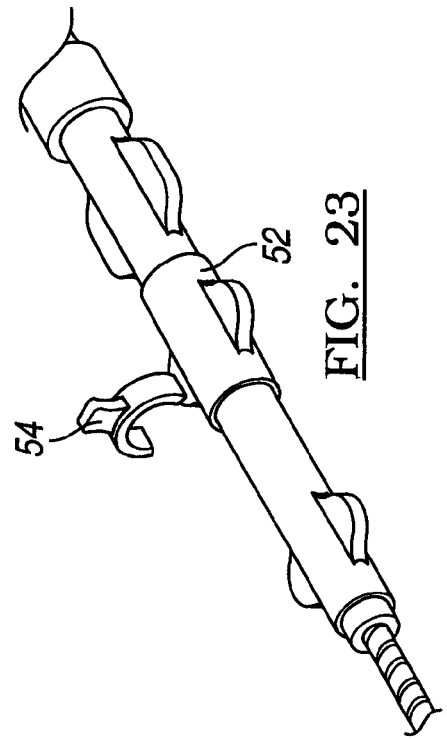
FIG. 23 depicts the safety mechanism in an "unlocked" position.
Figure 22:
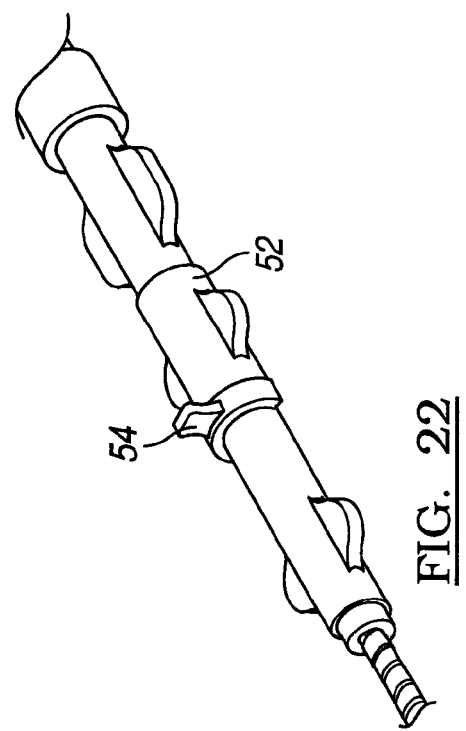
FIG. 22 depicts the safety mechanism in a "locked" position.

In this embodiment, the stiffening component 20 (FIG. 2) includes a helical tube 24 (FIGS. 19-20). Adjacent sections in its helical geometry can be opened or closed (compressed) to adjust the cross sectional stiffness of the inner tubular section 12 of the sheath assembly 2. As depicted in FIGS. 2 and 6-7, a linear path or track 30 is provided in the outer tube hub 16 which cooperates with the actuating mechanism or drive slide 18. As shown in FIGS. 2 and 8-9, the mechanism 18 is secured in a "soft" position.

Figure 4:
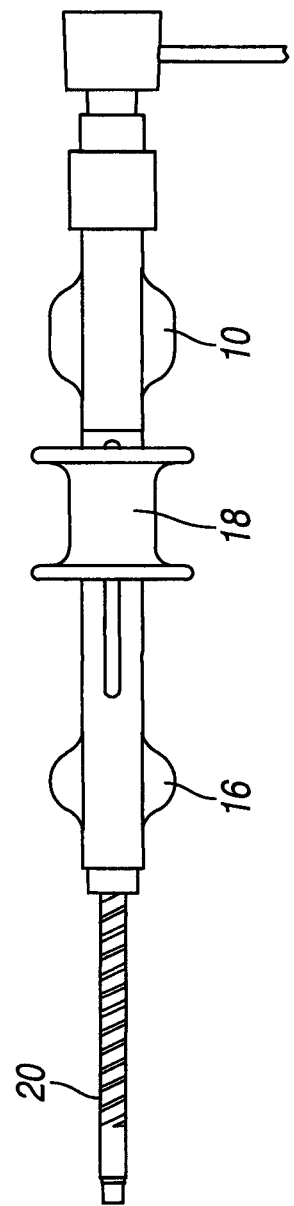
FIG. 4 depicts a proximal position of the sliding mechanism with a helical tube stiffening component (side elevational view)
Figure 11:
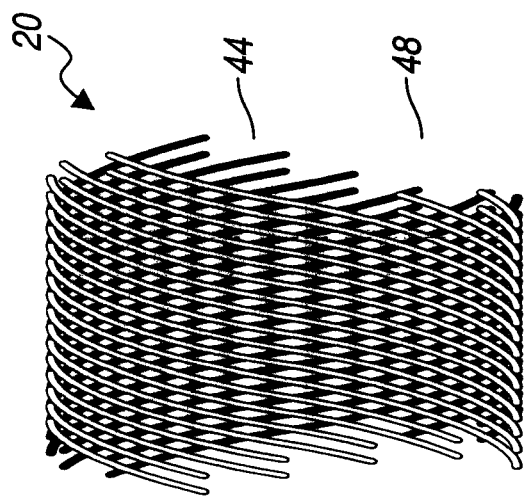
FIG. 11 depicts the braided wire or polymeric mesh in a closed (soft) configuration.

In FIGS. 3-4, the actuating mechanism 18 is depicted in a proximal position. FIG. 3 illustrates the outer tube 22. FIG. 4 illustrates a helical embodiment of the stiffening component 20, in which the helix is shown in an open position.

FIGS. 5-7 depict the actuating mechanism 18 in a distal, or "stiff" position. In FIG. 7, the helical tube stiffening component 20 is shown with the outer tube 22 hidden, and the helix is in a "closed" condition.

In one example, a proximal end region of the stiffening component 20 is attached to the actuating mechanism 18, which moves the stiffening component 20 distally and proximally in a linear motion. When the sliding mechanism 18 is in the proximal position, the helix is open, thereby creating a "soft" tubular section. When the sliding mechanism is in a distal position, the helix is closed, thereby creating a "stiff" tubular section.

In one embodiment, a suitable material for helical sections or strips of the tube stiffening component reinforcing member 20 is a polymer like TEFLON or a shape memory material, such as a nickel titanium alloy like NITINOL.

Locating features such as locking detents 38, 40 (FIGS. 8-9) can be provided in many forms. In one embodiment (FIG. 8) they are shown as a male/female hemispherical or arched form. They may also take the form of a snapping fixture on the actuating mechanism 18 which snaps into a mating detail in the outer tube hub 16. They may also take the form of a ratcheting-type design, with a pawl on the sliding mechanism 18 that locks into a ratcheting detail on the outer tube hub 16 or vice-versa. With either design, the pawl could be pressed and held open to return to the "soft" position. There are multiple ways to lock the sliding mechanism 18 in the "soft" and "stiff" positions. Only one form is shown in FIGS. 8-9.

In the embodiment of FIG. 9 the actuating mechanism 18 incorporates a tracking tab 42 which slides in a linear track 30 provided in the outer tube hub 16. The track 30 and tab 42 interface to permit a smooth motion and transition of linear force to the stiffening component 20. The stiffening component 20 can be fixed to the tracking tabs 42 on the sliding mechanism 18.

Additional design variations of the sliding mechanism 18 and tube stiffening component 20 are described below.

Embodiment #2

Braided Stiffening Component with Linear Slide

In this embodiment, the stiffening component 20 (FIGS. 10-13B) comprises a braided or stranded wire or mesh 44 arranged in a tubular configuration. The braided geometry is such that openings between the individual strands can be opened and closed through linear motion. The changing density of the open 46 and closed 48 positions adjusts the cross sectional stiffness of the tubular section of the component 20, thereby creating a "stiff" (FIG. 10) and "soft" (FIG. 11) condition.

Figure 10:
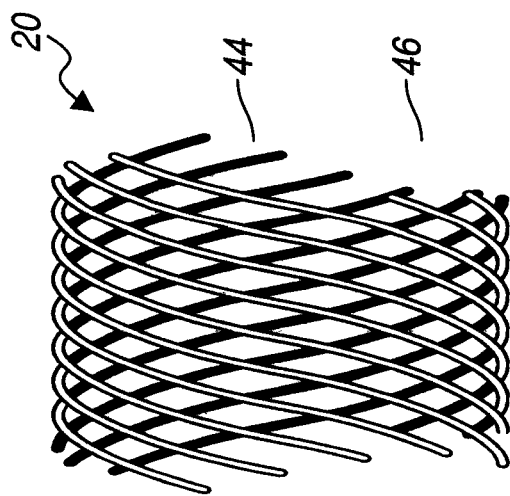
FIG. 10 depicts a braided wire or polymeric mesh in an open (stiff) position (Embodiment #2)
Figure 14:
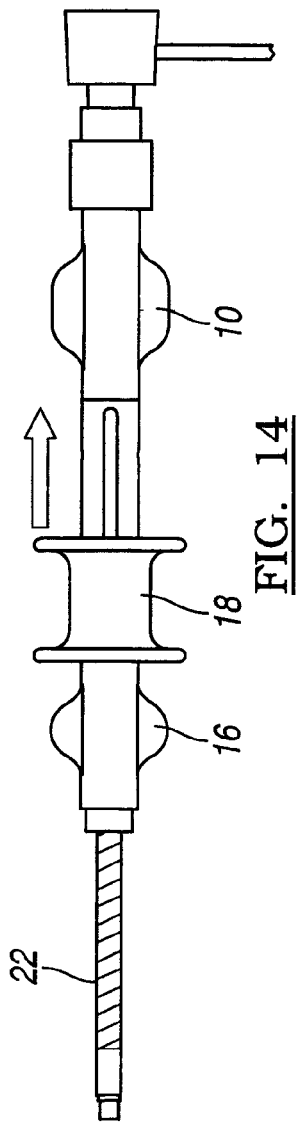
FIG. 14 depicts a distal position of the sliding mechanism, in which the outer tube is shown (side elevation view)
Figure 15A:
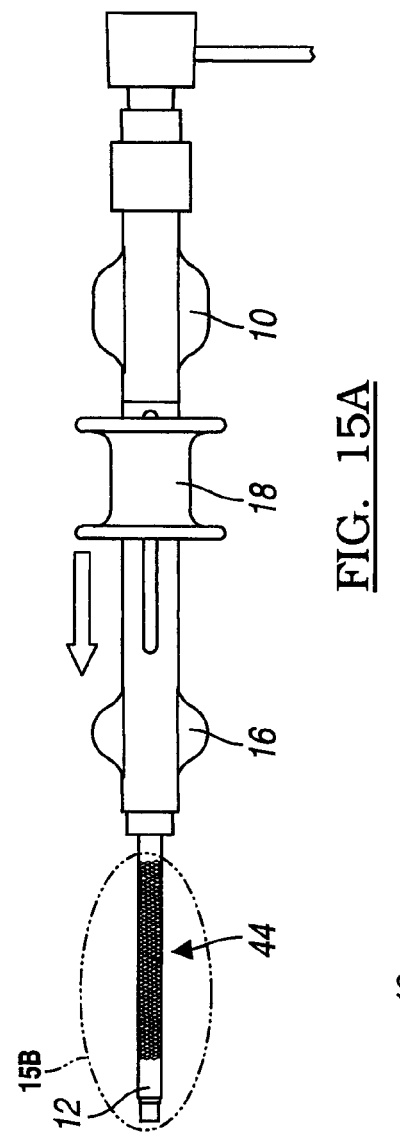
FIGS. 15A and 15B depict a proximal position of the sliding mechanism with the braided tube stiffening component, in which the outer tube is hidden (side elevation view)
Figure 15B:
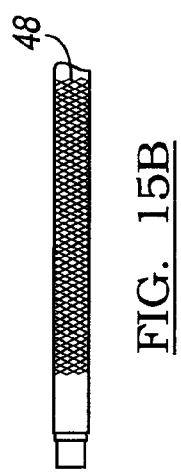

In one approach, the stiffening component 20 includes flexible strands of interwoven spirally-oriented filaments that form a cylindrical braid. As tension is applied to the stiffening component 20 by the actuating mechanism 18, the component 20 tends to become stiffer (FIG. 10). The component 20 in one embodiment optionally has an opening at each end that fits over the inner tube 12. The stiffening component 20 contracts radially as it is stretched longitudinally. In use, when a tensile force is applied to the proximal end of the stiffening component 20 and that force is opposed at the distal end so as to stretch the stiffening component 20, it will constrict in the transverse direction, thereby more tightly gripping the inner tube 12 as increasing longitudinal forces are applied. Preferably, the strands are made of a resilient, substantially non-elastic material such as a polymer or nickel-titanium alloy. Other materials such as a braided polymer (FIGS. 10-11) may also be deployed, additionally or alternatively. In cross-section, in one embodiment, the strands are helically positioned and each individual strand preferably has a circular or oval cross-section. Thus, the component 20 includes a cylindrical woven braid that has been drawn down snuggly upon and along at least a portion of the inner tube 12 by longitudinal tension.

As shown in FIGS. 10-15A, the proximal end 9 of the stiffening component 20 is attached to the actuating mechanism 18, which moves the stiffening component 20 distally and proximally in a linear motion. When the sliding mechanism 18 is in the proximal position (FIG. 10) the braided wire is open, thereby creating a "stiff" tubular section. When the sliding mechanism 18 is in the distal position, the braided strands are relatively closed (FIG. 11), thereby creating a "soft" tubular section. In FIGS. 13A, 13B, 15A, 15B, the outer tube 22 is hidden.

Embodiment #3

Rotational Sliding Mechanism

In this embodiment (FIGS. 16, 17), the actuating mechanism 18 is changed from linear motion to rotational or helical motion. Rotational motion can be used with the helical stiffening component 20 (Embodiment #1). Rotational motion will "wind up" the helix 50 of the tube stiffening component 20 (FIGS. 18-20), thereby changing its cross sectional stiffness.

In FIG. 16, the rotational handle 52 is shown in the "open" position. In FIG. 17, the rotational handle 52 is shown as having been rotated to a "closed" or "stiff" position.

Embodiment #4

Helical Actuating Mechanism

In this embodiment (FIGS. 18-20), motion of the actuating mechanism 18 is primarily helical. Helical displacement can be used with the helical tube stiffening component (Embodiment #1) and the braided tube stiffening component (Embodiment #2). The helical motion will "wind up" the helix 50 of the tube stiffening component 20, thereby changing its cross sectional stiffness. Linear motion 15 of the helical travel compresses and decompresses the braided wire 44, thereby changing its cross sectional stiffness.

Figure 18:
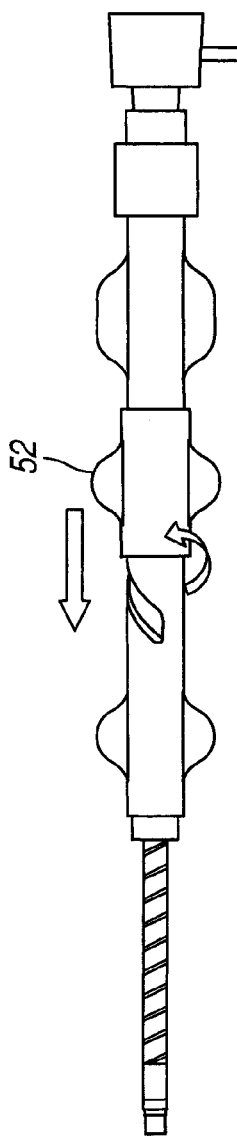
FIG. 18 depicts an "open" position ("soft") of the helical rotation handle (Embodiment #4, side elevation view)

In a preferred embodiment, helical motion of the sliding mechanism 18 is counterclockwise to accommodate a surgeon's desired practices. Most surgeons are trained to use a clockwise rotational motion when inserting a sheath into the vessel. By using a counterclockwise motion for stiffening the sheath, the potential for accidental engagement of the actuating mechanism 18 will be reduced. This is depicted in FIGS. 18-20. From FIG. 20, the drive slide 18 is removed. That figure is a more detailed view that depicts the helix 50 that is provided in the outer tube hub 16.

Figure 24:
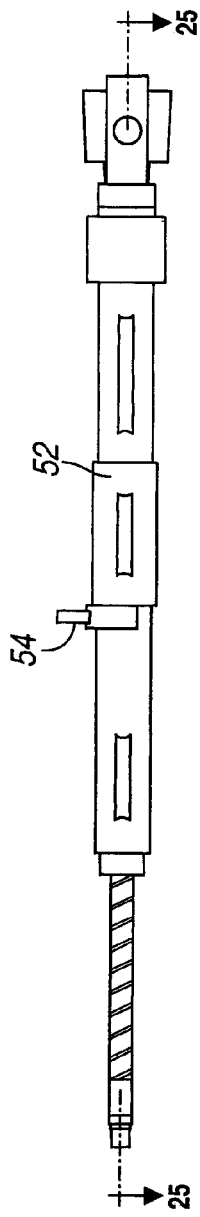
FIG. 24 is a side elevational view of the embodiment of FIG. 23.
Figure 25:
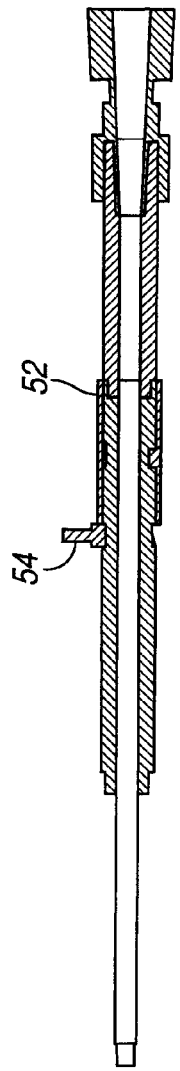
FIG. 25 is a longitudinal sectional view of the embodiment of FIG. 24 taken along the line 25-25 thereof.
Figure 26:
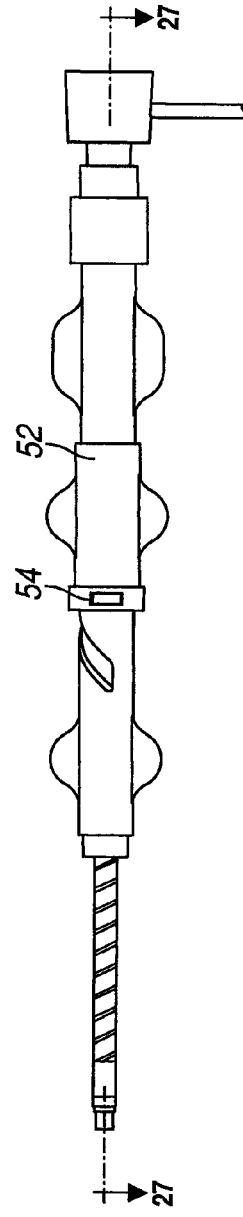
FIG. 26 is a top view thereof.
Figure 27:
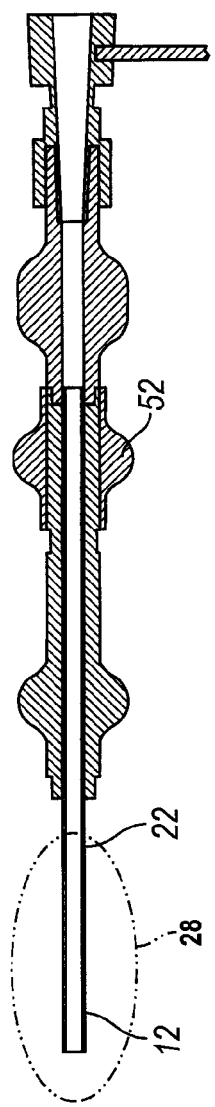
FIG. 27 is a sectional view of the embodiment of FIG. 26 taken along the line 27-27 thereof.

One form of a safety mechanism is depicted in FIGS. 21-26. To prevent accidental movement of the sliding mechanism 18, a safety feature 54 can optionally be incorporated into the rotational handle 52 or outer tube hub 16. The safety mechanism 54 could be incorporated into any of the design components, if desired. In the embodiment shown, the safety mechanism 54 is depicted as a removable, disposable component. In use, the safety mechanism 54 would be removed prior to operating the slide mechanism 18. A side view is depicted in FIG. 24; a sectional view of the side view is in FIG. 25; and a top view appears in FIG. 26; and a sectional view of the top view appears in FIG. 27, in which the safety feature 54 has been removed.

Figure 28:
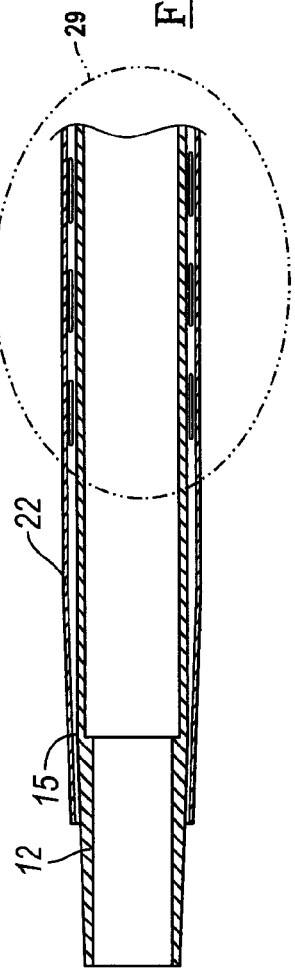
FIG. 28 depicts additional sectional detail of a distal end region of the shaft.
Figure 29:
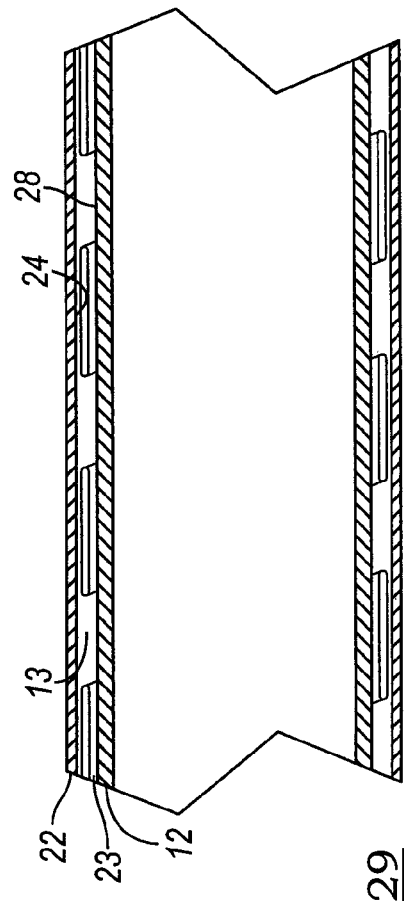
FIG. 29 is an enlarged portion thereof.

FIGS. 28-29 are cross sectional views that depict optional details of the distal end of the sheath assembly 2. Illustrated in FIGS. 28-29 are the inner tube 12, outer tube 22, helically cut tube 24, and the cavity 28 that lies between the inner and outer tubes. It will be appreciated that in FIG. 9, the helically cut tube 24 could be replaced in some embodiments by a braided form of stiffening component 20.

Depending on the application, alternative embodiments of the invention include sheaths that are for example 19, 23-25, 45, 50 or 65 cm in length. The length is selected based upon the insertion site and the anatomical area to be treated—e.g., insertion below the knee, the carotid artery, etc. Following is a list of reference numerals and the structural components to which they refer that are used in this disclosure:

| Reference Numeral | Component |
| --- | --- |
| 2 | Sheath assembly |
| 4 | Interventional devices |
| 6 | Valve system |
| 8 | Distal end |
| 9 | Proximal end |
| 10 | Inner tube hub |
| 12 | Inner tube |
| 13 | Outer surface of 12 |
| 14 | Valve assembly |
| 15 | Bond |
| 16 | Outer tube hub |
| 18 | Actuating (sliding) mechanism |
| 20 | Stiffening component |
| 22 | Outer tube |
| 23 | Inner surface of 22 |
| 24 | Helically cut tube |
| 26 | Inner tube lumen |
| 28 | Cavity between inner and outer tubes |
| 30 | Track in outer tube hub 16 for 18 |
| 32 | Locating feature |
| 34 | Locking position of 18 |
| 36 | Locking position of 18 |
| 38 | Locking detent (proximal) (soft) |
| 40 | Locking detent (distal) (stiff) |
| 42 | Tracking tab |
| 44 | Braided tube |
| 46 | Open position |
| 48 | Closed position |
| 50 | Helix of 20 |
| 52 | Rotational handle |
| 54 | Safety feature - removable clip |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An endovascular sheath apparatus comprising:
    an inner tube that includes an outer surface and an inner lumen, the inner lumen being substantially open between its distal and proximal ends and across its cross section before introducing medical fluids or devices so that they may pass along the inner lumen without interference;
    an outer tube with an interior surface, the outer surface of the inner tube and the interior surface of the outer tube defining a cavity therebetween;
    a stiffening component that is at least partially received in and may move in relation to the inner and outer tubes within at least part of the cavity outside the inner tube, the stiffening component having a distal end that is bonded to a distal end of the inner tube, the outer tube, or both, the stiffening component being selected from the group consisting of a braided material, interwoven spirally oriented filaments that form a cylindrical braid, a braided tube and a polymeric mesh; and an actuating mechanism that cooperates with a proximal end of the stiffening component, the stiffening component thus imparting to the inner tube and thus to the outer tube a stiffness characteristic that is influenced by a tensile force applied by the actuating mechanism, the actuating mechanism moving axially, rotationally or helically, the stiffness component thereby moving within the cavity without incursion into the inner lumen in response to axial, rotational, or helical displacement of the actuating mechanism, the actuating mechanism thereby adjusting the stiffness of the endovascular sheath.

2. The sheath apparatus of claim 1, further including:
an inner tube hub that is attached to a proximal end of the inner tube; and
a valve system detachably connected to the inner tube hub, the valve system including a one-way valve by which the medical fluids may be ducted into the inner tube, the valve preventing the flow of fluids out of the endovascular sheath, but allowing the introduction of interventional devices into the vasculature.

3. The sheath apparatus of claim 1, further comprising:
a bond between the stiffening component, the interior surface of the outer tube at a distal region of the outer tube and the outer surface of the inner tube, the bond providing a reaction region to axial, rotational forces or helical associated with deployment of the actuating mechanism and the stiffening component.

4. The sheath apparatus of claim 1, further including:
an outer tube hub that is attached to a proximal end of the outer tube, the outer tube extending through the outer tube hub.

5. The sheath apparatus of claim 4, wherein the outer tube hub includes:
a track that guides the actuating mechanism.

6. The sheath apparatus of claim 5, wherein the track and the actuating mechanism define one or more locating features that position the actuating mechanism and the stiffening component in relation to the outer tube hub, the locating features being selected from the group consisting of male-female hemispherical features and male-female arched features.

7. The sheath apparatus of claim 6, wherein the actuating mechanism optionally locks or moves into or through multiple positions provided by the locating features to provide a soft or stiff sheath or a sheath of intermediate stiffness.

8. The sheath apparatus of claim 5, wherein the track has a configuration that is selected from the group consisting of linear, helical, and combinations thereof.

9. The sheath apparatus of claim 5, wherein the actuating mechanism includes a handle that cooperates with the track by which longitudinal or rotational or combined longitudinal and rotational force can be applied to the actuating mechanism.

10. The sheath apparatus of claim 9, wherein the actuating mechanism includes a track that guides the handle in a counterclockwise direction for stiffening the sheath when viewed from a proximal end of the sheath apparatus.

11. The sheath apparatus of claim 4, further including a safety mechanism for preventing accidental movement of the actuating mechanism by impeding movement of the actuating mechanism, the safety mechanism including a clip that is detachably removable from a channel defined circumferentially in the outer tube hub.

12. The sheath apparatus of claim 1, wherein the actuating mechanism upon moving axially distally, rotationally or helically applies tension and thus stiffens the stiffening component.

13. The sheath apparatus of claim 1, wherein the stiffening component comprises a material selected from the group consisting of a braided material, interwoven spirally oriented filaments that form a cylindrical braid, a braided tube, a braided wire, a polymeric mesh, stranded metal, a stranded polymer, and a helical tube braided material is selected from the group consisting of metal, strands of plastic materials, stranded wire, mesh arranged in a tubular configuration and a braided polymer, such that the braided material becomes stiffer under tension.

14. The sheath apparatus of claim 1, wherein the stiffening component includes a shape memory material.

15. The sheath apparatus of claim 14, wherein the shape memory material includes a nickel-titanium alloy.

16. The sheath apparatus of claim 1, wherein the interwoven spirally oriented filaments include a criss-crossing array that defines a generally cylindrical surface.

17. The sheath apparatus of claim 16, wherein the cylindrical surface has an internal diameter that decreases in response to a longitudinal force that is applied in tension to the stiffening component.

18. The sheath apparatus of claim 1, wherein the stiffening component provides a differential level of stiffness along the length of the sheath.

19. The sheath apparatus of claim 1, wherein there is a changing modulus of elasticity along the length of the sheath.

20. The sheath apparatus of claim 19, wherein the actuating mechanism enables the modulus of elasticity to be discretely or gradually changed along the length of the sheath.

21. The sheath apparatus of claim 1 wherein an outside diameter of the outer tube is less at its distal end than at its proximal end.

22. A method of guiding a sheath through a vascular passageway, the method comprising the steps of:
(A) providing the sheath with
an inner tube that includes an open lumen along substantially its entire length and diameter through which medical fluids or devices can be introduced without interference;
an outer tube having an interior surface, the outer and interior surfaces defining a cavity therebetween;
a stiffening component that is received in and may move within the cavity, the stiffening component having a distal end that is bonded to a distal end of the inner tube, the outer tube, or both, the stiffening component being selected from the group consisting of a braided material, interwoven spirally oriented filaments that form a cylindrical braid, a braided tube, a polymeric mesh, the braided material being selected from the group consisting of metal, strands of plastic materials, stranded wire, mesh arranged in a tubular configuration and a braided polymer;
an actuating mechanism that cooperates with a proximal end of the stiffening component, the stiffening component being made more stiff by axial tension applied by the actuating mechanism and thus imparting to the inner tube and thus to the outer tube a stiffness characteristic that is influenced by the actuating mechanism, the actuating mechanism moving axially, rotationally or helically, the stiffness component thereby moving within the cavity without incursion into the lumen of the inner tube in response to axial, rotational, or helical displacement of the actuating mechanism, the actuating mechanism thereby adjusting the stiffness of the endovascular sheath;
(B) inserting a proximal end of the sheath into a vascular structure; and (C) adjusting the stiffness of at least a portion of the sheath by applying an axial force to the stiffening component, the stiffening component being located coaxially over the inner tube of the sheath to selectively stiffen at least a portion of the inner tube.

23. The method of claim 22 wherein the adjusting step comprises stiffening the inner tube when additional column strength is needed to overcome an obstruction or constriction in the vascular passageway.

24. The method of claim 22 wherein the adjusting step comprises increasing the stiffness of the inner tube by applying an axial force in tension to the stiffening component to reduce buckling of the sheath when the sheath is being pushed through a tortuous part of the vascular system.

25. The method of claim 22 wherein the amount of axial force is varied while the sheath is being pushed through the vascular passageway.

26. A method of assembling an endovascular sheath, comprising steps of:
   (A) providing an inner tube that includes an open lumen along substantially its entire length and diameter through which medical fluids or devices can be introduced without interference;
   (B) surrounding the inner tube with an outer tube having an interior surface, the outer and interior surfaces defining a cavity therebetween;
   (C) positioning a stiffening component within the cavity, the stiffening component having a distal end that is bonded to a distal end of the inner tube, the outer tube, or both and comprising a material selected from the group consisting of a braided material, interwoven spirally oriented filaments that form a cylindrical braid, a braided tube, a polymeric mesh, the braided material being selected from the group consisting of metal, strands of plastic materials, stranded wire, mesh arranged in a tubular configuration and a braided polymer;
   (D) positioning an actuating mechanism that cooperates with a proximal end of the stiffening component, the stiffening component imparting to the inner tube a stiffness characteristic that is influenced by the actuating mechanism; and
   (E) moving the actuating mechanism axially, rotationally or helically, the stiffness component thereby moving within the cavity without incursion into the lumen of the inner tube in response to axial, rotational, or helical displacement of the actuating mechanism, the actuating mechanism thereby adjusting the stiffness of the endovascular sheath.

* * * * *